(12) United States Patent
Patel et al.

(10) Patent No.: US 6,589,973 B1
(45) Date of Patent: Jul. 8, 2003

(54) PREPARATION OF SELECTIVE CYCLOOXYGENASE II INHIBITORS

(75) Inventors: Dinesh Shantilal Patel, West Bengal (IN); Sachin Dinesh Patel, Maharashtra (IN); Shashikant Prabhudas Kurani, Maharashtra (IN)

(73) Assignee: THEMIS Medicare Ltd. (IN)

( * ) Notice: Subject to any disclaimer, the term of this patent is extended or adjusted under 35 U.S.C. 154(b) by 0 days.

(21) Appl. No.: 10/146,674

(22) Filed: May 15, 2002

(51) Int. Cl.⁷ .................. A61K 31/415; A61K 31/44
(52) U.S. Cl. .................. 514/406; 514/334; 514/403; 514/404; 514/407; 514/602; 514/604; 514/605; 514/777; 514/471; 514/473
(58) Field of Search ................. 514/334, 403, 514/404, 406, 407, 471, 473, 602, 604, 605, 777

(56) References Cited

U.S. PATENT DOCUMENTS 5,466,823 A * 11/1995 Talley et al. ............ 548/377.1

\* cited by examiner

*Primary Examiner*—Frederick Krass
(74) *Attorney, Agent, or Firm*—Pendorf & Cutliff

(57) ABSTRACT

A clear, stable novel pharmaceutical preparation of selective cyclooxygenase II inhibitors (COX 2) inhibitors in the parenteral form for the treatment of pain & inflammatory conditions arising because of cyclooxygenase-2 activity. In particular the pharmaceutical preparation of COX 2 inhibitors comprise of selective active COX 2 inhibitors selected from Celeoxib, Rofecoxib and their analogs dissolved in a selective isosorbide type solvent of following general formula I

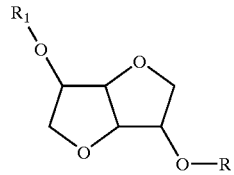

FORMULA I where $R_1$ and $R_2$ are hydrogen or alkyl chains containing 1–3 carbons or acetate group. Also disclosed is a simple and cost effective process of manufacture of the above novel pharmaceutical preparation.

18 Claims, No Drawings

PREPARATION OF SELECTIVE CYCLOOXYGENASE II INHIBITORS

BACKGROUND OF THE INVENTION

FIELD OF THE INVENTION

This invention relates to a clear, stable novel pharmaceutical preparation of selective cyclooygeiase II inhibitors (COX 2) inhibitors preferably in the parenteral form for the treatment of pain & inflammatory conditions arising because of cyclooxygenase-2 activity.

DESCRIPTION OF THE RELATED ART

Selective COX 2 inhibitors like Celecoxib, Rofecoxib and their analogs have been widely indicated for the treatment of mucoskeletal disorders such as rheumatoid arthritis, osteoarthritis, ankylosing spondylitis and for the management of acute pain. They have also been indicated for primary treatment of dysmenorrhea. Chronic treatment of patients with Rofecoxib and Celecoxib has been effective in suppressing the inflammation without causing gastric toxicity which is normally associated with non selective NSAID (Simon et al, 1998, 1999; Bensen et al 1999 Emery et al 1999; Howaky et al 2000, Schintzer et al 1999; Ehlidrich et al 1999; Laine eta al 1999 through Goodman & Gilman's The pharmacological basis of therapeutics $10^{th}$ edition, McGraw Hill Medical Publication Division 2001).

WO 0145705 and WO 0145706 teaches preparation of oral formulations of celecoxib.

WO 0069434 and WO 0032189 discloses solid dosage forms of COX2 inhibitors modified by mixing the same with excipients to achieve a metter availability of the drug as a oral dosage formulation.

Publication WO 0048583 is directed to again an oral dosage formulation of Rofecoxib with 5HT antigonists.

WO 0032189 published yet further celecoxib composition for oral consumption as a sustained release dosage form for the treatment of cycloxygenase mediated disorders.

Thus all the presently available selective COX 2 inhibitors are either prepared as oral tablets and/or oral liquid suspensions. Although easy to administer, oral dosage forms delay the onset of the desired pharmacological action due to the amount of time this route of administration takes to achieve the required plasma concentrations of the drug. As a result of this, the selective COX 2 inhibitors have a significant lag time before the onset of therapeutic effect. Additionally, the intake of food even further influences this drug absorption and hence the time taken for the onset of action. It has also been reported that some of these selective COX 2 inhibitors decrease the therapeutic concentration by a further 20% when taken along with Antacids.

Due to these above limitations, selective COX 2 inhibitors in parenteral form capable of instant therapeutic action are extremely desirable. In order to prepare parenteral formulations of these class of compounds, a suitable carrier/vehicle is required in which these drugs are soluble. Obviously, this carrier/vehicle need to be safe and non-toxic. Due to the physiochemical properties of these groups of compounds, selective COX 2 inhibitors like Celecoxib, Rofecoxib, Valdecoxib, Itacoxib and Deracoxib are poorly soluble in water hence presenting a difficulty in formulating these drugs in the parenteral form.

Attempts to provide COX-2 Inhibitors like Celecoxib and Rofecoxib or analogs in parenteral form using various solvents viz., Alcohols, Dimethyl Sulphoxide, Propylene Glycol and Glycerin were found to be unsuccessful either due to problems of solubility or that when these drugs dissolve in solvents like Isopropenol Acid mixture, Dimethyl Sulphoxide and Propylene Glycol the concentration range for the therapeutic administration of the above drugs through intramuscular route does not permit the above solvent usage as they are found to be toxic.

Due to such problems it has not been possible to have injectable formulation of Celecoxib, Rofecoxib, Valdecoxib, Etoricoxib or Deracoxib. The only injection available is in the form of Paracoxib which is a pro-drug of Valdecoxib and is available as a sodium salt. Paracoxib when administered parentally, is hydrolysed to Valdecoxib after reaching the blood stream.

It is known that paranteral administration is always beneficial for quick onset of action for the anti-inflammatory/analgesic activity. This is because quick action on body when drug is administered, concentration of the drug has to reach maximum level in the blood to achieve the therapeutic effect and this is achievable by injectable preparation than by oral preparation. Oral preparations when administered takes concentration time to reach blood level as it has to undergo first-pass metabolism.

Thus although there has been a need in the art for injectable forms of COX-2 inhibitors for direct parenteral administration it could not be achieved because of the above discussed limitation of solubility and problems of toxicity.

OBJECT OF THE INVENTION

It is thus the basic object of the present invention to provide a stable pharmaceutical preparation of selective COX 2 inhibitors such as Rofecoxib or Celecoxib or analogs preferably in parenteral form capable of instant therapeutic action which would avoid the above discussed limitations of obtaining COX 2 inhibitors in parenteral form.

Another object is directed to provide injectable pharmaceutical preparation of selective COX 2 inhibitor such as Rofecoxib or Celecoxib or analogs preferably in parenteral form which would be simple and cost-effective to obtain.

Yet further object of the present invention is directed to provide injectable pharmaceutical preparation of selective COX 2 inhibitor such as Rofecoxib or Celecoxib or analogs preferably in parenteral form which would be stable, clear, limpid and easily administrable intramuscularly and would be safe having instant therapeutic activity vis-à-vis the presently available oral tablets/liquid formulations of COX 2 inhibitors.

Yet further object of the present invention is directed to provide pharmaceutical preparation of selective COX 2 inhibitor such as Rofecoxib or Celecoxib or analogs in gel form.

SUMMARY OF THE INVENTION

It has been found by way of the present invention that injectable formulations of COX 2 inhibitors can be obtained of COX 2 inhibitors only when dissolved in a selective isosorbide type solvent of following general formula I.

FORMULA I

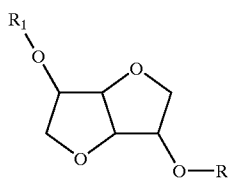

where $R_1$ and R are hydrogen or alkyl chains containing 1–3 carbons or acetate group.

Thus according to one aspect of the present invention there is provided a stable pharmaceutical preparation such as for parenteral administration of COX 2 inhibitors comprising of selective active COX 2 inhibitors selected from Celecoxib, Rofecoxib and their analogs dissolved in a selective isosorbide type solvent of following general formula I.

FORMULA I

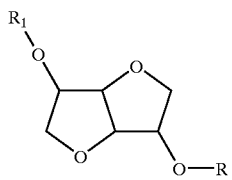

where $R_1$ and R are hydrogen or alkyl chains containing 1–3 carbons or acetate group.

The formulation of the invention above can optionally contain water and/or one or more antioxidants.

This solution is clear and limpid and can be easily administered intramuscularly with the desired therapeutic dose. This formulation is stable, safe and effective. In certain cases, it is even better than the presently widely used anti-inflammatory drugs like Diclofenac sodium injection administered by intramuscular route.

In accordance with one embodiment the formulation of the selective active Rofecoxib is prepared by selectively dissolving Rofecoxib in Isosorbide type solvent with or without water.

In accordance with another embodiment the formulation of the selective Celecoxib is prepared by selectively dissolving Celecoxib in Isosorbide type solvent preferably containing antioxidants. The addition of an antioxidant like alpha tocopherol and/or its derivatives enhances the stability of the Celecoxib preparation.

In acordance with a preferred aspect of the invention the pharmaceutical preparation comprising the injection of Celecoxib can be prepared in the strength of 1 mg/ml to 500 mg/ml in said solvent DMI.

In acordance with another preferred aspect of the invention the pharmaceutical preparation comprising the injection of Rofecoxib can be prepared in the strength of 1 mg/ml to 50 mg/ml in said solvent DMI.

In both said injectable forms of the pharmaceutical preparation of the invention optionally anti-oxidants like Sodium bisulphate or Vit.E can be incorporated.

In accordance with yet another aspect of the invention the Celecoxib and Rofecoxib preparations can be provided in the form of Gel using the same solvent in the strength of 1% to 4% for local applications with or without other ingredients such as carbomer derivatives, HPMC (hydroxy propyl methyl cellulose), gelatine, sodium CMC, water and flavouring agent.

In accordance with another aspect the present invention also relates to process for manufacturing of the parenteral preparation of COX 2 inhibitor preferably for parenteral administration comprising
i) selectively providing a COX 2 inhibitor selected from Rofecoxib, celecoxib and analogous thereof; and
ii) dissolving the said selected COX 2 in a selective isosorbide type solvent of general formula I

FORMULA I

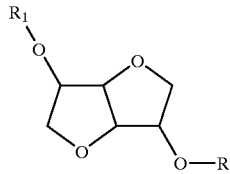

where $R_1$ and R are hydrogen or lower alkyl chains containing 1–3 carbons or acetate groups and optionally water/ and one or more antioxidants.

The present invention further relates to the use of the above described parenteral preparation for the treatment of pathological conditions associated with rheumatoid arthritis and osteoarthritis and for the treatment of primary dysmenorrhea in which composition comprising of the selective actives Celecoxib, Rofecoxib, their analogs and compound of general formula I.

FORMULA I

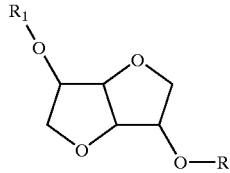

wherein $R_1$ and R are hydrogen or lower alkyl chains containing 1–3 carbons or acetate and optionally water/and one or more antioxidants.

The compound of Formulae I is preferably 2,5-di-O-methyl-1, 4:3,6 dianhydro-D-glucitol.

DETAILS OF THE INVENTION

The compounds represented by the general formula I are selectively identified as an excellent solvent for Celecoxib, Rofecoxib and their analogs. It has been surprisingly found that the solubility of Celecoxib and Rofecoxib in the selective compounds of general formula I, avoid the problems of preparation of liquid/parenteral formulations of COX 2 inhibitors. The parenteral formulation prepared by dissolving Celecoxib (with and without the presence of an antioxidant) and Rofecoxib in compounds represented by formula I can be safely used for the treatment of inflammation and the pathological condition associated and mediated because of Cyclooxygenase II and for its inhibition.

Addition of upto 20% water to the above mentioned parenteral preparation of Rofecoxib does not alter the physical or chemical stability of the preparation.

Also, it was observed that the addition of an antioxidant like alpha tocopherol (upto 0.1%) to the above mentioned parenteral preparation of Celecoxib results in a very stable solution with no change in characteristic over extended period of time.

The details of the invention, its objects and advantages are explained hereunder in greater detail in relation to non-limiting exemplary illustrations of its preparation hereunder:

EXAMPLE 1

3.976 mmol of Rofecoxib was added to 100 ml of 2,5-di-O-methyl-1, 4:3,6 dianhydro-D-glucitol while stirring. The solution was stirred further for 15 minutes in an aseptic condition. This solution was filtered aseptically and filled and sealed in vials/ampoules.

EXAMPLE 2

3.976 mmol of Rofecoxib was added to 80ml of 2,5-di-O-methyl-1, 4:3,6 dianhydro-D-glucitol while stirring. The solution was stirred further in aseptic condition and 20 ml of injectable grade water was added. This solution (diluted to 100 ml with of 2,5-di-O-methyl-1, 4:3,6 dianhydro-D-glucitol) was then filtered aseptically, filled and sealed in vials/ampoules.

EXAMPLE 3

7.952 mmol of Rofecoxib was added to 80ml of 2,5-di-O-methyl-1, 4:3,6 dianhydro-D-glucitol while stirring. The solution was stirred further in aseptic condition and 20ml of injectable water was added. This solution (diluted to 100 ml with of 2,5-di-O-methyl-1, 4:3,6 dianhydro-D-glucitol) was filtered aseptically, filled and sealed in vials/ampoules.

EXAMPLE 4

26.22 mmol of Celecoxib was added to 100 ml of 2,5-di-O-methyl-1, 4:3,6 dianhydro-D-glucitol while stirring. This solution was stirred further for 15 minutes in an aseptic condition. This solution was filtered aseptically and filled and sealed in vials/ampoules.

EXAMPLE 5

26.22 mmol of Celecoxib and 0.116 mmol (0.05% w/v) alpha tocopherol were added to 100 ml of 2,5-di-O-methyl-1, 4:3,6 dianhydro-D-glucitol while stirring. The solution was stirred for a further 15 minutes. The solution was then filtered aseptically, filled and sealed in vials/ampoules.

EXAMPLE 6

26.22 mmol of Celecoxib and 0.232 mmol (0.1% w/v) alpha tocopherol were added to 100 ml of 2,5-di-O-methyl-1, 4:3,6 dianhydro-D-glucitol while stirring. This solution was stirred further for 15 minutes in aseptic condition. The solution was then filtered aseptically, filled and sealed in vials/ampoules.

EXAMPLE 7

52.44 mmol of Celecoxib and 0.116 mmol(0.05 w/v) of alpha tocopherol (Vitamin E) were added to 100 ml di-O-methyl-1, 4:3,6 dianhydro-D-glucitol while stirring. This solution was stirred further for 15 minutes in aseptic conditions. The solution was then filtered aseptically, filled and sealed in vials/ampoules.

EXAMPLE 8

52.44 mmol of Celecoxib and 0.232 mmol (0.1% w/v) alpha tocopherol was added to 80 ml of 2,5-di-O-methyl-1, 4:3,6 dianhydro-D-glucitol while stirring. The solution is stirred further for 15 minutes in aseptic condition. The solution was then filtered aseptically, filled and sealed in vials/ampoules.

The efficacy, pharmacokinetic profile and stability studies were further carried out in respect of the injectable parenteral form of the COX-2 inhibitors in accordance with the invention as detailed hereunder:

EXAMPLE-I

The efficacy of the parenteral formulations according to the invention was next studied vis-à-vis the conventional voveran injection formulation as detailed by way of the following experimental illustrations:

Method: Carrageenan induced rat paw edema
Animals used: Albino rats (Wistar)
Number of animals used: 6 per group
Dose of Rofecoxib Inj.: 2.25 mg/kg, Dose of Celecoxib Inj.: 18 mg/kg
Dose of Control Voveran (Diclofenac sodium –4.5 mg/kg
Route of administration: Intra-muscular
Method:

Albino rats of either sex were divided into three groups each containing six animals each. First group was used as control and received Voveran diclofenac sodium (4.5 mg/kg) and served as the standard group. The second group was administered the formulation of Rofecoxib Intra-muscular injection at a single therapeutic dose of 2.25 mg/kg. The third group was administered the formulation of Celecoxib Intra-muscular injection at a single therapeutic dose of 18 mg/kg.

Fifteen minutes after the administration of the compound, carrageenan (0.1 ml of 0.1% solution in saline) was injected into subplantar region of the hind paw of each rat. Immediately the paw volume was measured. The paw volume was then measured 30 min, 1, 3 and 4 hr. after carrageenan administration. The difference between initial and subsequent reading gave the edema volume for the corresponding time. The % inhibition for the respective compound on an hourly basis was calculated on the basis of the following formula:

$$\% \; INHIBITION = \frac{V \; untreated - V \; treated}{V \; untreated} \times 100$$

V: Volume of mercury displacement

The mean reduction in edema values obtained are reproduced in Table A, B and C hereunder:

TABLE A

Observations (Volume of Mercury Displacements in ml)

| Voveran Injection | Mean Reduction in edema | | | | |
|---|---|---|---|---|---|
| | 0 hr | 0.5 hr | 1 hr | 3 hr | 4 hr |
| Dose - 4.5 mg/kg | 6.74% | 22.75% | 27.87% | 43.25% | 43.58% |

TABLE B

| Rofecoxib Injection | Mean Reduction in edema | | | | |
|---|---|---|---|---|---|
| | 0 hr | 0.5 hr | 1 hr | 3 hr | 4 hr |
| Dose - 2.25 mg/kg | 5.13% | 19.74% | 25.78% | 40.00% | 35.35% |

TABLE C

|  | Mean Reduction in edema | | | | |
|---|---|---|---|---|---|
| Celecoxib Injection | 0 hr | 0.5 hr | 1 hr | 3 hr | 4 hr |
| Dose - 1.55 mg/kg | 1.55% | 18.45% | 23.34% | 37.5% | 35.35% |

It was observed that animals in the Diclofenac group showed about 43.25% mean reduction in the edema at the end of 3 hours whereas the mean reduction in edema with Rofecoxib formulation was 40% and with Celecoxib formulation, the edema inhibition was found to be 37.5% with respect to comparative values of the control groups at the end of 3 hours.

Thus it could be concluded that both the test formulations of Rofecoxib and Celecoxib Intra-muscular Injections of the invention exhibited good anti-inflammatory activity in the therapeutic concentration with encouraging comparable data as compared to the marketed formulation Voveran (Diclofenac sodium 25 mg/ml).

EXAMPLE-IIA

Comparative Pharmacokinetic Profile of Celecoxib Injection Vis-à-Vis Celecoxlb Capsules Protocol Followed:
I) Pharmacolmnetic Studies of CelecoxIb I. M. Injection 100 mg/ml in Rabbits Rabbits (n=3) would be kept on overnight fasting before the start of the experimentation on the preceding morning. Fasting blood samples would be collected (0hr.). No food will be given for 2 hrs. Thereafter, each subject would receive a single dose of Celecoxib.

The following blood sampling design would be adopted for Celecoxib I.M. Injection:
5 ml of blood would be collected at intervals of 10 min., 15 min., 20 min., 30 min., 1 hr., 1.5 hr., 2 hr., 3 hr and 4 hr after the drug administration.
BLOOD SAMPLES:
5 ml of venous blood samples collected would be centrifuged for 15 min. at 3000 RPM in order to obtain plasma immediately. The plasma will be transferred into Icon 2054, 23×75 mm tubes and frozen at −20° C. until the time analysis. All samples will be properly labeled with the adhesive tapes identifying the subject's number, date and the collection time relative to the drug administration and the study number.
PLASMA ANALYSIS
The plasma levels of the test will be analyzed by reverse phase HPLC. The drug quantity per ml of plasma will be calculated using a standard graph of concentration vs. AUC by adding known quantities of Celecoxib.
PHARMACOKINETIC ANALYSIS:
The following pharmacokinetic parameters will be estimated:
1) $C_{max}$: Maximum plasma concentration attained
2) $T_{max}$: Time at which maximum concentration is attained
3) AUC: Area Under the plasma-concentration curve.
4) $K_{el}$: Mean elimination rate constant
5) $t_{1/2}$: Mean half life elimination
6) Relative Pharmacokinetic Profiles using Standard Reference
7) In-vitro-in-vivo co-relation II) Pharmacokinetic Study of Celecoxib Oral Capsules 100 mg/caps. In Rabbits
EXPERIMENTAL PROTOCOL:
Rabbits (n=3) would be kept on overnight fasting before the start of the experimentation on the preceding morning. Fasting blood samples would be collected (0hr.). No food will be given for 2 hrs. Thereafter, each subject would receive a single dose of Celecoxib.

The following blood sampling design would be adopted for Celecoxib Oral Capsules:
5 m of blood would be collected at intervals of 0 min., 15 min., 30 min., 1 hr., 2 hr., 4 hr., 5 hr., 6 hr and 8 hrs after the drug administration.
BLOOD SAMPLES:
5ml of venous blood samples collected would be centrifuged for 15 min. at 3000 RPM in order to obtain plasma immediately. The plasma will be transferred into Icon 2054, 23×75mm tubes and frozen at −20° C. until the time analysis. All samples will be properly labeled with the adhesive tapes identifying the subject's number, date and the collection time relative to the drug administration and the study number.
PLASMA ANALYSIS
The plasma levels of the test will be analyzed by reverse phase HPLC. The drug quantity per ml of plasma will be calculated using a standard graph of concentration vs. AUC by adding known quantities of Celecoxib.
PHARMACOKINETIC ANALYSIS:
The following pharmacokinetic parameters will be estimated:
1) Cmax: Maximum plasma concentration attained
2) Tmax: Time at which maximum concentration is attained
3) AUC: Area Under the plasma-concentration curve.
4) Kel: Mean elimination rate constant
5) t1/2: Mean half life elimination
6) Relative Pharmacokinetic Profiles using Standard Reference Results achieved are provided hereunder in Table D

TABLE D (Rabbit Model)

| | TIME CONCENTRATION VALUE OF CELECOXIB INJECTION | | TIME CONCENTRATION VALUE OF CELECOXIB CAPSULES | |
|---|---|---|---|---|
| SR. NO. | TIME | Cmax VALUES (ng) | TIME | Cmax VALUES (ng) |
| 1. | 0 min | Not detected | 0 min | Not detected |
| 2. | 15 min | 4421 (±70) | 15 min | 185 (±11) |
| 3. | 30 min | 2583 (±79) | 30 min | 329 (±17) |
| 4. | 1 hr | 2144 (±101) | 1 hr | 823 (±21) |
| 5. | 2 hr | 1634 (±93) | 2 hr | 568 (±11) |
| 6. | 3 hr | 1007 (±37) | 3 hr | 509 (±27) |
| 7. | 4 hr | 915 (±64) | 4 hr | 435 (±31) |

EXAMPLE IIB

Comparative Pharmacokinetic Profile of Rofecoxib Injection/Rofecoxib Capsules

I) Pharmacokinetic Studies of Rofecoxib I.M. Injection 12.5 mg/ml in Rabbits
EXPERIMENTAL PROTOCOL:
Rabbits (n=3) would be kept on overnight fasting before the start of the experimentation on the preceding morning. Fasting blood samples would be collected (0 hr.). No food will be given for 2 hrs. Thereafter, each subject would receive a single dose of Rofecoxib.

The following blood sampling design would be adopted for Rofecoxib I.M. Injection:

5ml of blood would be collected at intervals of 10 min., 15 min., 20 min., 30 min., 1 hr., 1.5 hr., 2 hr., 3 hr and 4 hr after the drug administration.

BLOOD SAMPLES:

5ml of venous blood samples collected would be centrifuged for 15 min. at 3000 RPM in order to obtain plasma immediately. The plasma will be transferred into Icon 2054, 23×75 mm tubes and frozen at −20° C. until the time analysis. All samples will be properly labeled with the adhesive tapes identifying the subject's number, date and the collection time relative to the drug administration and the study number.

PLASMA ANALYSIS

The plasma levels of the test will be analyzed by reverse phase HPLC. The drug quantity per ml of plasma will be calculated using a standard graph of concentration vs. AUC by adding known quantities of Rofecoxib.

PHARMACOKINETIC ANALYSIS:

The following pharmacokinetic parameters will be estimated:
1) Cmax: Maximum plasma concentration attained
2) Tmax: Time at which maximum concentration is attained
3) AUC: Area Under the plasma-concentration curve.
4) Kel: Mean elimination rate constant
5) t1/2: Mean half life elimination
6) Relative Pharmacokinetic Profiles using Standard Reference
7) In-vitro-in-vivo co-relation II) Pharmacokinetic Study of Rofecoxib Oral Capsules 12.5 mg/caps. In Rabbits

EXPERIMENTAL PROTOCOL:

Rabbits (n=3) be kept on overnight fasting before the start of the experimentation on the preceding morning. Fasting blood samples would be collected (0 hr.). No food will be given for 2 hrs. Thereafter, each subject would receive a single dose of Rofecoxib.

The following blood sampling design would be adopted for Rofecoxib Oral Capsules:

5 ml of blood would be collected at intervals of 0 min., 15 min., 30 min., 1 hr., 2 hr., 4 hr., 5 hr., 6 hr and 8 hrs after the drug administration.

BLOOD SAMPLES:

5 ml of venous blood samples collected would be centrifuged for 15 min. at 3000 RPM in order to obtain plasma immediately. The plasma will be transferred into Icon 2054, 23×75 mm tubes and frozen at −20° C. until the time of analysis. All samples will be properly labelled with the adhesive tapes identifying the subject's number, date and the collection time relative to the drug administration and the study number.

PLASMA ANALYSIS

The plasma levels of the test will be analyzed by reverse phase HPLC. The drug quantity per ml of plasma will be calculated using a standard graph of concentration vs. AUC by adding known quantities of Celecoxib.

PHARMACOLMNETIC ANALYSIS:

The following pharmacokinetic parameters will be estimated:
1) Cmax: Maximum plasma concentration attained
2) Tmax: Time at which maximum concentration is attained
3) AUC: Area Under the plasma-concentration curve.
4) Kel: Mean elimination rate constant
5) t1/2: Mean half life elimination
6) Relative Pharmacokinetic Profiles using Standard Reference Results obtained are provided hereunder in Table E

TABLE E (Rabbit Model)

| | TIME CONCENTRATION VALUE OF ROFECOXIB INJECTION | | TIME CONCENTRATION VALUE OF ROFECOXIB CAPSULES | |
|---|---|---|---|---|
| SR. NO. | TIME | Cmax VALUES (ng/ml) | TIME | Cmax VALUES (ng/ml) |
| 1. | 0 min | Not detected | 0 min | Not detected |
| 2. | 10 min | 1240 (±0.21) | 10 min | 374 (±0.09) |
| 3. | 15 min | 2950 (±0.33) | 15 min | 431 (±0.01) |
| 4. | 30 min | 1020 (±0.14) | 30 min | 568 (±0.12) |
| 5. | 1 hr | 312 (±0.05) | 1 hr | 878 (±0.08) |
| 6. | 2 hr | 82 (±0.009) | 2 hr | 849 (±0.18) |
| 7. | 3 hr | 39 (±0.04) | 3 hr | 624 (±0.02) |
| 8. | 4 hr | 24 (±0.001) | 4 hr | 415 (±0.065) |

EXAMPLE-IIIA

Studies Were Carried Out to Evaluate the Central Analgesic Activity of Celecoxib Injection I.M. (100 mg/ml) of the Invention Protocol followed:

Albino rats of either sex (150–200 g) were divided in four groups consists of six animals in each group. Group I received the vehicle and served as control. Group II received the standard drug (Pentazocin; Fortwin injection 30 mg/ml). Group III received the test drug Celecoxib Injection I.M. (100 mg/ml) at comparative human dose of 200 mg (4 mg).

The animals were placed on a hot plate maintained at 55° C. Latency (time taken to lick the hind paw i.e. reaction time) was recorded before and after IM administration of the standard and the test drugs. Before administration of the drug, initial time taken to lick the hind paw i.e. basal reaction time (BRT) was recorded. Formulations were administered 20 minutes prior to placement on the hot plate and then after 20 min, time taken to lick the hind paw i.e. latent reaction time (LTR) was recorded 6 The percent increase in reaction time was calculated as follows % Increase in reaction time=LRT−BRT×100 BRT Data obtained was subjected to the statistical analysis using Dunnet 't' test.

0% Increase in Reaction Time=LRT−BRT×100 BRT

Dose in Rats=Human Dose×0.02 200 mg×0.02−4 mg i.e 4000 mcg

TABLE F

COMPARATIVE DATA ON MEAN BASAL REACTION TIME, LATENT REACTION TIME AND PERCENT INCREASE IN REACTION TIME (n = 6)

| Sr. No. | Group | Basal Reaction Time (BRT) Sec | Latent Reaction Time (LRT) Sec | % Increase in Reaction Time (IRT) |
|---|---|---|---|---|
| 1 | Control | 6.83 ± 0.75 | 6.83 ± 0.75 | 0 |
| 2 | Standard (Pentazocin 20 mcg/kg) | 6.33 ± 0.41 | 11.66 ± 1.60 | 92.85 |
| 3 | Test (Celecoxib Injection I.M.; 100 mg/ml); 4000 mcg | 5.66 ± 0.79 | 15.83 ± 2.20 | 184.4 |

Each value mean (S.E.M.; P < 0.001, Dunnet 't' test.

EXAMPLE: IIIB

Studies Were Carried Out to Evaluate the Central Analgesic Activity of Rofecoxib Injection I.M. (12.5 mg/ml) of the Invention Protocol Followed:

Albino rats of either sex (150–200 g) were divided in four groups consists of six animals in each group. Group I received the vehicle and served as control Group II received the standard drug (Pentazocin; Fortwin injection 30 mg/ml). Group III received the test drug Rofecoxib Injection I.M. (12.5 mg/ml) at comparative human dose of 12.5 mg (0.25 mg).

The animals were placed on a hot plate maintained at 55° C. Latency (time taken to lick the hind paw i.e. reaction time) was recorded before and after IM administration of the standard and the test drugs. Before administration of the drug, initial time taken to lick the hind paw i.e. basal reaction time (BRT) was recorded. Formulations were administered 20 minutes prior to placement on the hot plate and then after 20 min, time taken to lick the hind paw i.e. latent reaction time (LTR) was recorded.[6] The percent increase in reaction time was calculated as follows % Increase in reaction time=LRT−BRT×100 BRT
Data obtained was subjected to the statistical analysis using Dunnet 't' test.

% Increase in Reaction Time=LRT−BRT×100 BRT
Dose in Rats=Human Dose×0.02 12.5 mg×0.02=0.25 mg i.e. 250 mcg Results obtained are provided hereunder:

TABLE G

COMPARATIVE DATA ON MEAN BASAL REACTION TIME, LATENT REACTION TIME AND PERCENT INCREASE IN REACTION TIME (n = 6)

| Sr. No. | Group | Basal Reaction Time (BRT) Sec | Latent Reaction Time (LRT) Sec | % Increase in Reaction Time (IRT) |
|---|---|---|---|---|
| 1 | Control | 6.83 ± 0.75 | 6.83 ± 0.75 | 0 |
| 2 | Standard (Pentazocin 20 mcg/kg) | 6.33 ± 0.41 | 11.66 ± 1.60 | 92.85 |
| 3 | Test (Rofecoxib Injection I.M.; 100 mg/ml); 4000 mcg | 4.16 ± 0.36 | 11.83 ± 0.79 | 193.05 |

Each value represents mean ± S.E.M.; $P < 0.01$, Dunnet 't' test.

RESULTS

It would be apparent from Tables F and G above that Clecoxib Injection (100 mg/ml) as well as the Rofecoxib Injection (12.5 mg/ml) in accordance with the present invention demonstrated significant central analgesic activity as compared to control. Celecoxib/Rofecoxib formulation was found to be statistically superior in comparison to the standard drug Pentazocin ($P<0.001$). The study with respect to Hot Plate Analgesometer in rats revealed the central analgesic activity similar to that possessed by opioid analgesics. Celecoxib/Rofecoxib formulations of the invention can be useful in situations where opioid analgesic were used. Thus Celecoxib/Rofecoxib formulation of the invention can be useful for moderate to severe pain, and also be advantageous over opioid analgesics having limitations with respect to their addictions liability and respiratory depression.

EXAMPLE-IV

Stability Studies on Parenteral Formulations Obtained in Accordance with the Invention

FOR CELECOXIB

For the purpose parenteral formulation of celecoxib was obtained following the procedure as detailed under Example 6 above in these batches (Samples A, B & C) wherein the constitutions are I100 mg of celecoxib dissolved in 1 ml of dimethylisosorbide with one set of the three samples obtained using antioxident alpha tocophenol (Vit E) and another set of three samples obtained without any such antioxident.

The study was carried out as per ICH guidelines for a time period of upto to 3 months. The concentration of drug was estimated by using isocratic conditions on GBC, HPLC equipment, $C_{18}$ column, 220 nm and 20 μl. The results are as below in Tables H and I.

TABLE H

| Celecoxib Injection with Vit. E 0.1% w/v Result in % of theoretical concentration | Concentration 100 mg/ml pH 5.2 | | |
|---|---|---|---|
| | Initial | 3 months at 25° ± 2° C./60% ± 5% RH | 3 months at 40° ± 2° C./75% ± 5% RH |
| Sample A | 100.9% | 100.3% | 100.1% |
| Sample B | 99.6% | 99.3% | 99.06% |
| Sample C | 101.01% | 100.1% | 99.8% |

RH - Relative Humidity

TABLE I

| Celecoxib Injection with Vit. E in % of theorEtical concentration | Concentration 100 mg/ml pH 5.2 | | |
|---|---|---|---|
| | Initial | 3 months at 25° ± 2° C./60% ± 5% RH | 3 months at 40° ± 2° C./75% ± 5% RH |
| Sample A | 99.8% | 99.3% | 99% |
| Sample B | 100.3% | 100.0% | 99% |
| Sample C | 99% | 98.3% | 97.8% |

FOR ROFECOXIB

The stability of three batches of Rofecoxib parenteral formulation (samples A, B & C) obtained in accordance with the invention was tested. Each said sample was obtained involving Rofecoxib solution containing 20% water wherein 12 mg of Rofecoxib was dissolved in dimethylisosorbide to have a total volume of 1 ml in which 0.2 ml is water.

The study was carried out as per ICH guidelines for a time period of upto to 3 months. The concentration of drug was estimated by using isocratic conditions on GBC, HPLC equipment, $C_{18}$ column, 220 nm and 20 μl. The results are as below in Tables J.

TABLE J

Stability Test

Rofecoxib Injection
Results in % of theoratical
amount of Rofecoxib

Concentration  12.5 mg/ml
pH             5.20

| | With 20% water | | | Without 20% water | | |
|---|---|---|---|---|---|---|
| | Initial | 6 months at 25° ± 2° C./ 60% ± 5% RH | 6 months at 40° ± 2° C./ 75% ± 5% RH | Initial | 6 months at 25° ± 2° C./ 60% ± 5% RH | 6 months at 40° ± 2° C./ 75% ± 5% RH |
| Sample A | 100.3% | 100.1% | 99.98% | 100.8% | 100.3% | 100.15% |
| Sample B | 99.96% | 99.35% | 99.15% | 100.75% | 100.3% | 99.9% |
| Sample C | 99.6% | 98.78% | 99.0% | 99.9% | 99.75% | 99.3% |

The above results confirm the stability of the pharmaceutical preparation in accordance with the invention.

What is claimed is:

1. A pharmaceutical preparation comprising selective active COX 2 inhibitors selected from celecoxib, rofecoxib or their analogs dissolved in a selective isosorbide solvent of following general formula I

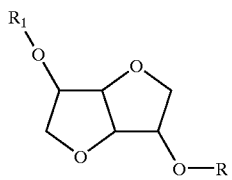

FORMULA I where $R_1$ and R are hydrogen or alkyl containing 1–3 carbons or acetate group.

2. A pharmaceutical preparation according to claim 1, further comprising other pharmaceutically acceptable additives.

3. A pharmaceutical preparation according to claim 2, further comprising at least one of water and one or more antioxidants.

4. A pharmaceutical preparation according to claim 1, wherein the said solvent of general formula I is 2,5-di-O-methyl-1, 4:3,6 dianhydro-D-glucitol.

5. A pharmaceutical preparation according to claim 1, wherein the concentration of celecoxib is 1 mg/ml to 500 mg/ml.

6. A pharmaceutical preparation according to claim 5, wherein the concentration of celecoxib is 1 mg/ml to 400 mg/ml.

7. A pharmaceutical preparation according to claim 1, wherein the concentration of rofecoxib is about 1 mg/ml to 50 mg/ml.

8. A pharmaceutical preparation according to claim 7, wherein the concentration of rofecoxib is 1 mg/ml to 25 mg/ml.

9. A pharmaceutical preparation according to claim 3, wherein said antioxidant is selected from the group consisting of alpha tocopherol, its derivatives, sodium bisulphate, and vitamin E.

10. A pharmaceutical preparation according to claim 1, wherein said pharmaceutical preparation is contained in a sealed ampoule, vial, bottle, capsule, tube or any other container.

11. A pharmaceutical preparation according to claim 1, formulated for parenteral administration for instant treatment of pain and inflammatory condition arising from cyclooxygenase-2 activity.

12. A pharmaceutical preparation according to claim 1, wherein said pharmaceutical preparation is in gel form.

13. A pharmaceutical preparation according to claim 12 in gel form for local applications comprising said selective active COX 2 inhibitors in said solvent in the strength of 1% to 4% and optionally other ingredients selected from the group consisting of carbomer derivatives, HPMC (hydroxy propyl methyl cellulose), gelatine, sodium CMC, water and flavoring agents.

14. A process for manufacturing a preparation of COX 2 inhibitor suitable for parenteral administration comprising i) providing a COX 2 inhibitor selected from rofecoxib, celecoxib or analogs thereof; and ii) dissolving the COX 2 inhibitor in a selective isosorbide solvent of general formula I

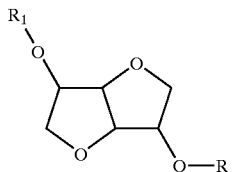

FORMULA I where $R_1$ and R are hydrogen or alkyl containing 1–3 carbons or acetate groups and optionally water/and one or more antioxidants.

15. A process according to claim 14, comprising adding pharmaceutically acceptable additives.

16. A process according to claim 14, wherein said solvent of formula I is 2,5-di-O-methyl-1, 4:3,6 dianhydro-D-glucitol.

17. A method for forming a stable pharmaceutical preparation of COX 2 inhibitors, said method comprising dissolving a COX 2 inhibitor selected from celecoxib, rofecoxib or their analogs in a selective isosorbide solvent of general formula I

FORMULA I

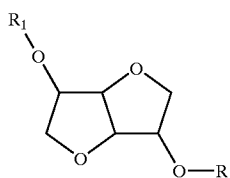

where $R_1$ and R are hydrogen or alkyl containing 1–3 carbons or acetate.

18. A method for treating COX-2 mediated disorders, comprising administering to a mammal in need thereof a pharmaceutical preparation comprising celecoxib, rofecoxib or their analogs dissolved in an isosorbide solvent of the general formula:

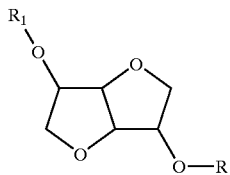

wherein $R_1$ and R are hydrogen or alkyl containing 1–3 carbons or an acetate group.

* * * * *